United States Patent [19]

Fujii et al.

[11] 4,418,012
[45] Nov. 29, 1983

[54] LEUCYLALANY-ARGININE DERIVATIVE

[75] Inventors: Setsuro Fujii, Toyonaka; Mamoru Sugimoto, Sakura; Takashi Yaegashi, Funabashi, all of Japan

[73] Assignee: Torii & Co. Ltd., Tokyo, Japan

[21] Appl. No.: 300,415

[22] Filed: Sep. 9, 1981

[30] Foreign Application Priority Data

Sep. 16, 1980 [JP] Japan .................. 55-128271

[51] Int. Cl.$^3$ .......................................... C07C 103/52
[52] U.S. Cl. ............................................ 260/112.5 R
[58] Field of Search ................................. 260/112.5 R

[56] References Cited

U.S. PATENT DOCUMENTS

| | | | |
|---|---|---|---|
| 3,886,136 | 5/1975 | Claeson et al. | 260/112.5 R |
| 4,137,225 | 1/1979 | Af Ekenstam et al. | 260/112.5 R |
| 4,252,715 | 2/1981 | Aurell et al. | 260/112.5 R |
| 4,257,940 | 3/1981 | Fujii et al. | 260/112.5 R |
| 4,308,201 | 12/1981 | Fujii et al. | 260/112.5 R |
| 4,308,202 | 12/1981 | Fujii et al. | 260/112.5 R |

*Primary Examiner*—Delbert R. Phillips

*Attorney, Agent, or Firm*—Beveridge, DeGrandi and Kline

[57] ABSTRACT

A leucylalanyarginine derivative represented by the formula,

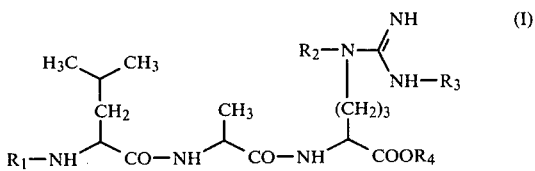

wherein $R_1$ represents hydrogen or an amino-protecting group; $R_2$ and $R_3$ represent hydrogen or guanidino-protecting groups; and $R_4$ represents naphthyl. The above compound is useful as an excellent substrate for various enzymes, such as trypsin, plasmin, kallikrein, urokinase, Cl-esterase and the like. Accordingly, the activity of enzymes can be measured by use of said compound as a substrate.

6 Claims, 1 Drawing Figure

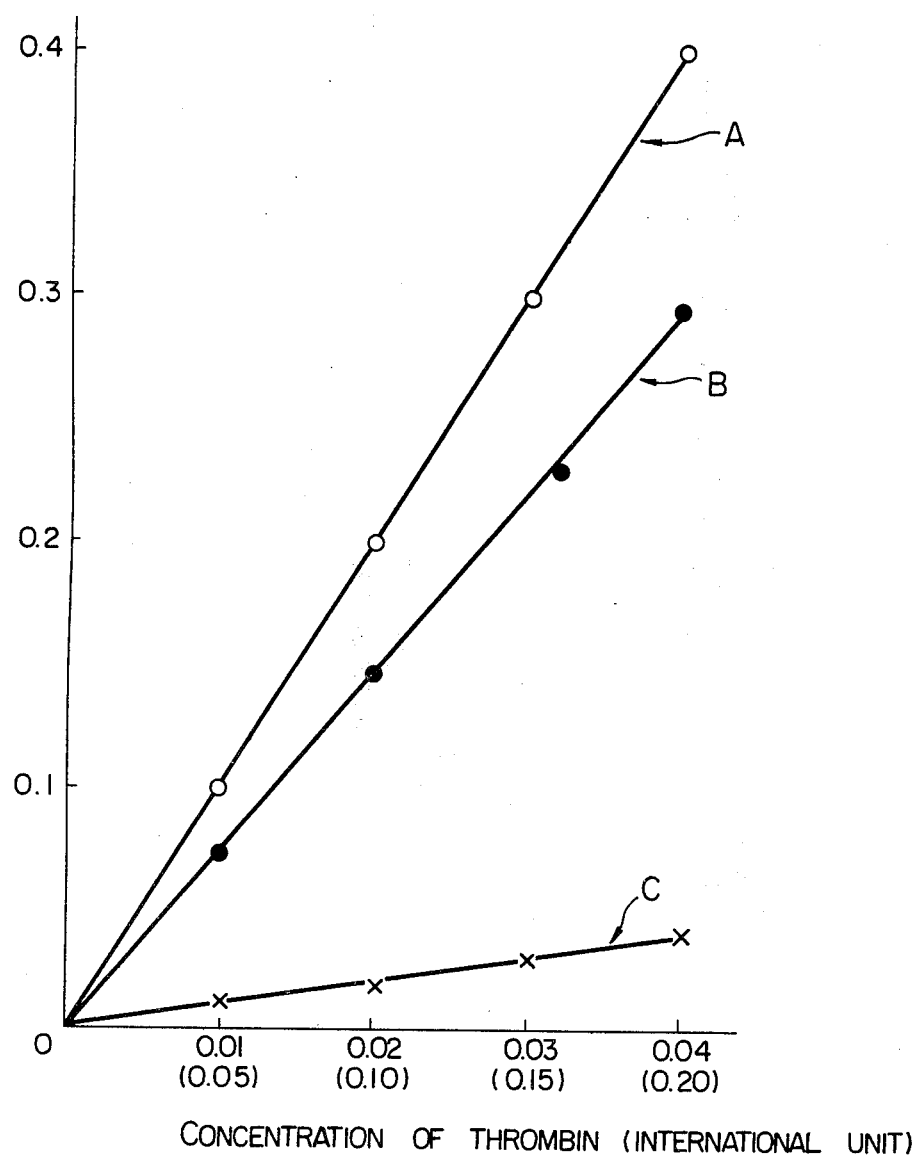

LEUCYLALANYLARGININE DERIVATIVE

This invention relates to a novel leucylalanylarginine derivative, a process for producing the same, and a method for measuring the activity of enzymes using the compound as a substrate.

Hitherto, many methods have been known for measuring the activity of enzymes. One of them is a method by which an alkyl ester of an amino acid is contacted as a substrate with an enzyme and the activity of the enzyme is determined from the degree of hydrolysis of the alkyl ester. For example, the well-known Hestrin method is one of the methods. This is a method which comprises contacting an enzyme with an alkyl ester of an amino acid, converting the remaining ester group after a given period of time with hydroxylamine into a hydroxamic acid, allowing it to react with ferric chloride to develop a color, and measuring the color as an absorbance, and determining the enzyme's ability to hydrolyze the ester, namely the activity of enzyme, from the absorbance.

In addition, there is a method in which para-nitroanilide of an amino acid is used as a substrate and the ability to hydrolyze the same is used as an index, or the like. In these methods, a considerable about of an enzyme is required, and when the enzyme concentration is low or when the enzyme has a low activity, it has been difficult to measure the activity of enzyme.

The present inventors have conducted extensive research on compounds satisfying the following three conditions: They have an affinity to an enzyme, the determination of the amount of enzyme is easy, and the detective sensitivity of the compounds is good. Consequently, the inventors have found compounds useful as substrate which are very excellent as to the above conditions as compared with the conventional ones, and a simple method for measuring the activity of enzyme by use of the compounds.

An object of this invention is to provide a novel amino acid derivative which is useful as an excellent substrate for an enzyme.

Another object of this invention is to provide a process for producing the said novel amino acid derivative.

A further object of this invention is to provide a method for measuring the activity of an enzyme by use of said novel amino acid derivative as a substrate for the enzyme.

Other objects and advantages of this invention will become apparent from the following description.

According to this invention, there is provided a leucylalanylarginine derivative represented by the formula,

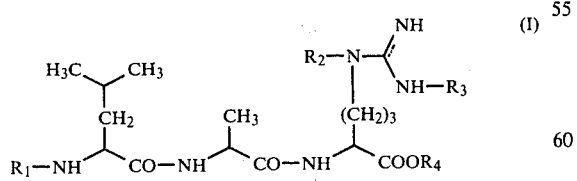

wherein $R_1$ represents hydrogen or an amino-protecting group; $R_2$ and $R_3$ represent hydrogen or guanidino-protecting groups and $R_4$ represents naphthyl.

This invention further provides a process for producing a leucylalnaylarginine derivative represented by the formula (I), which comprises subjecting to dehydration-condensation a compound (II) represented by the formula,

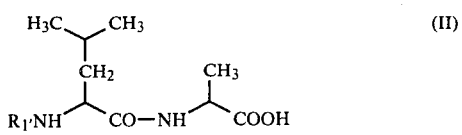

wherein $R_1$ represents an amino-protecting group, and an arginine derivative (III) represented by the formula,

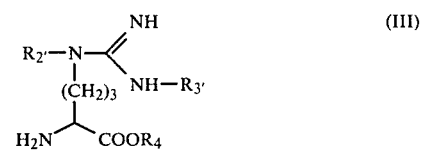

wherein $R_{2'}$ and $R_{3'}$ represent guanidino-protecting groups and $R_4$ represents naphthyl, in a conventional manner to obtain a compound (IV) represented by formula,

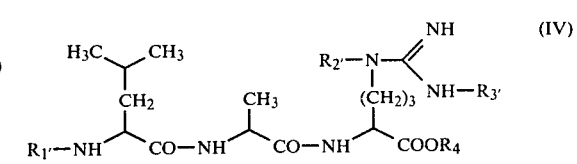

wherein $R_{1'}$, $R_{2'}$, $R_{3'}$ and $R_4$ have the same meanings as defined above, and then, if necessary, removing the amino-protecting group and/or the guanidino-protecting groups from the compound (IV) in a conventional manner.

According to this invention, there is also provided a method for measuring the activity of an enzyme, which comprises contacting the enzyme with a leucylalanylarginine derivative represented by the formula (I) as a substrate.

The starting compound (II) used in the production of the compound (I) of this invention may be a commercially available one or may be prepared by condensing a compound (V) represented by the formula,

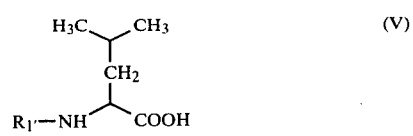

wherein $R_{1'}$ has the same meaning as defined above, with a compound represented by the formula,

wherein $R_5$ represents alkyl, into an ester (VII) represented by the formula,

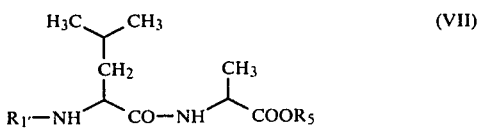

wherein $R_{1'}$ and $R_5$ have the same meanings as defined above, and then hydrolyzing the ester (VII).

The starting arginine derivatives (III) includes $N^\delta, N^\omega$-dibenzyloxycarbonyl-L-arginine 1-naphthyl ester and the like, and may be prepared by naphthylating an arginine derivative (III') having a suitable protecting group represented by the formula,

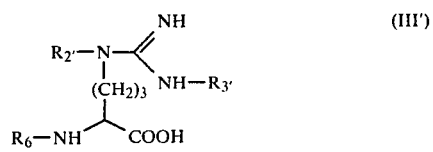

wherein $R_{2'}$ and $R_{3'}$ have the same meanings as defined above, and $R_6$ represents an amino-protecting group different from the $R_{2'}$ and $R_{3'}$ groups, to form a compound (III'') represented by the formula,

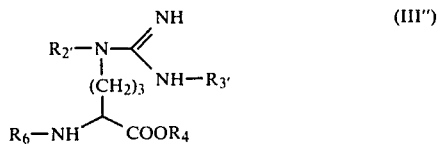

wherein $R_{2'}$, $R_{3'}$, $R_4$ and $R_6$ have the same meanings as defined above, and then selectively removing only the amino-protecting group in the α-position from the compound (III'').

In the formulas (I), (II), (III), (III'), (III''), (IV), (V), and (VII), the amino-protecting group includes protecting groups which are conventionally used in the synthesis of a peptide, such as t-butyloxycarbonyl, benzyloxycarbonyl, acetyl, benzoyl, tosyl and the like, among which acetyl and benzoyl are preferred, and the guanidino-protecting group includes nitro, tosyl, benzyloxycarbonyl or the like, or the guanidino group may form an acid-addition salt by proton-addition, among which benzyloxycarbonyl is preferred.

In the production of the compound (IV), the compound (II) and the arginine derivative (III) are dissolved in a suitable solvent, and to the resulting solution is added an activating agent which is usually used, such as dicyclohexylcarbodimide (DCC), diphenylphosphorylazide (DPPA), an alkyl chlorocarbonate or the like, after which, if necessary, a base such as triethylamine or the like is added thereto and the resulting mixture is stirred, thereby preparing the compound (IV). The solvent used includes conventional solvents, such as chloroform, dichloromethane, dimethylformamide, tetrahydrofuran and the like as far as the starting materials can be dissolved therein. The reaction temperature may be within the range of 0° to 40° C.

After the completion of the reaction, the compound (IV) can be isolated from the reaction mixture by a conventional treatment. That is to say, when DCC is used as the activating agent, the dicyclohexylurea (DCU) precipitated is removed by filtration, and a suitable extracting solvent such as ethyl acetate is added to the filtrate, after which the extract is washed with an aqueous citric acid solution, saturated aqueous sodium bicarbonate solution and saturated aqueous sodium chloride solution, dried over anhydrous magnesium sulfate, and then evaporated under reduced pressure to remove the solvent to obtain the compound (IV).

The amino-protecting group and/or the guanidino-protecting groups of the compound (IV) is removed in a conventional manner. That is to say, when the amino-protecting group and the guanidino-protecting groups are benzyloxycarbonyl, the compound (IV) is dissolved in a suitable solvent and a catalyst such as palladium-carbon or the like is added to the resulting solution to remove the protecting group or groups reductively, or the compound (IV) is added to a solution of hydrobromic acid in acetic acid and the hydrobromide of the objective compound precipitated is taken out by filtration, whereby the compound (I) is obtained.

The compound (I) of this invention is useful as an excellent substrate for various enzymes such as trypsin, plasmin, kallikrein, urokinase, Cl-esterase, thrombin and the like. That is to say, when the compound (I) of this invention is contacted with an enzyme, the compound serves as a substrate, and naphthol is liberated by hydrolysis with the enzyme after a given period of time, after which the amount of naphthol is measured to determine the activity of the enzyme. The fact that the activity of an enzyme can be measured easily is very important for quantitative analysis of an enzyme preparation, diagnosis by measuring the enzyme pattern in blood, diagnosis by measuring the enzyme concentration in blood or urine, or the like.

When the activity of an enzyme is measured according to the method of this invention, the enzyme is contacted with a given amount of the compound (I) of this invention in a suitable buffer solution, and after a given period of time at a given temperature, the amount of naphthol liberated is measured, thereby determining the activity of the enzyme. The buffer solution may be a suitable one having the optimum pH for the enzyme. The reaction may be effected under suitable constant conditions as to temperature and time, though it is preferable to measure the amount of the naphthol liberated at a temperature of 25° to 37° C. after 30 min.

The measurement of the amount of naphthol may be conducted by any of the known methods, for example, a physicochemical method, such as, gas chromatography, thin layer chromatography, or the like; or a chemical method, such as, ferric chloride reaction, diazo-coupling reaction, a Fast Violet B salt (FVB) method, or the like, though a method which comprises adding FVB to the reaction mixture to develop a color and measuring the absorbance by means of a photometer is more preferable in view of simplicity and detection sensitivity.

When the activity of thrombin is measured by use of benzoyl-L-leucylalanyl-L-arginine 1-naphthyl ester as a substrate according to the method of this invention, the sensitivity thereof is about 50 times that of Nα-tosyl-L-arginine methyl ester or benzoylarginine ethyl ester as used in the Hestrin method.

The amount of the naphthol measured by the method of this invention corresponds to the activity or amount of the enzyme.

According to the method of this invention, it is possible to detect a change in enzyme concentration in blood or urine due to various diseases with ease.

This invention is further illustrated below referring to Examples and the accompanying drawings, which shows standard curves of the concentration of thrombin in which the ordinate indicates absorbance and the abscissa indicates the amount (international unit) of thrombin, provided that the numbers in the parentheses refer to the amount of thrombin in the case of Nα-tosylarginine methyl ester. Curve A refers to leucylalanylarginine naphthyl ester, Curve B to benzoylleucylalanylarginine naphthyl ester, and Curve C to Nα-tosylarginine methyl ester.

EXAMPLE 1

Production of L-leucyl-L-alanyl-arginine 1-naphthyl ester p-toluenesulfonate

In 15 ml of N,N-dimethylformamide (DMF) were dissolved 1.01 g of benzyloxycarbonyl-L-leucyl-L-alanine and 2.05 g of $N^\delta,N^\omega$-dibenzyloxycarbonyl-L-arginine 1-naphyl ester trifluoroacetate, after which 742 mg of DCC, 446 mg of 1-hydroxybenzotriazole (HOBt) and 0.41 ml of triethylamine (TEA) were added to the solution with ice-cooling. The resulting mixture was stirred at the same temperature for 3 hrs and then stirred at room temperature for 24 hrs. After the reaction, the DCU thus precipitated was removed by filtration, and ethyl acetate was added to the filtrate. The resulting mixture was washed with 10% citric acid solution, saturated sodium bicarbonate solution and saturated sodium chloride solution in this order, dried over anhydrous magnesium sulfate, and then evaporated under reduced pressure to remove the solvent. The residue thus obtained was absorbed on a silica gel column, and purified with chloroform containing 0.3% by weight of methanol. The purified residue was recrystallized from chloroform-diethyl ether to obtain 1.2 g (yield 4.5%) of a white powder of benzyloxycarbonyl-L-leucyl-L-alanyl-$N^\delta,N^\omega$-dibenzyloxycarbonyl-L-arginine 1-naphthyl ester, m.p. 179°–183° C.

IR $\nu_{max}^{KBr}$ cm$^{-1}$: 3400, 3250, 1740, 1715, 1640.

NMR δ ppm (CDCl$_3$+DMSO—d$_6$): 0.9 (6H, d,

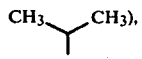

1.3 (3H, d,

1.7 (6H, b, —CH$_2$—), 2.0 (3H, b, >CH$_2$, >CH—), 4.2 (3H, b,

5.1 (4H, s,

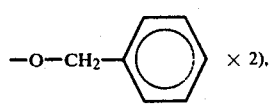

5.3 (2H, s,

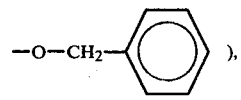

7.2–8.2 (22H, m, aromatic protons).

In 10 ml of DMF was dissolved 886 mg of the above ester, and 100 mg of 5% palladium-carbon (Pd-C) and 571 mg of p-toluenesulfonic acid monohydrate were added to the solution. The resulting mixture was stirred for 2 hrs while passing hydrogen gas therethrough, after which the Pd-C was removed by filtration. To the filtrate was added anhydrous diethyl ether, and the white powder thus precipitated was collected to obtain 690 mg (yield 83%) of L-leucyl-L-alanyl-L-arginine 1-naphthyl ester p-toluenesulfonate, m.p. 71° C.-(decomp.)

IR $\nu_{max}^{KBr}$ cm$^{-1}$: 3400, 1750, 1650.

NMR δ ppm (DMSO-d$_6$): 0.9 (6H, b,

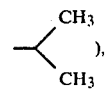

1.3 (3H, d, CH$_3$—CH—), 1.3–2.3 (7H, b, —CH$_2$—, —CH—), 3.2 (2H, b, —CH$_2$—NH—), 4.0–4.8 (3H, b,

7.2–8.2 (17H, m aromatic protons).

EXAMPLE 2

Production of benzoyl-L-leucyl-L-alanyl-L-arginine 1-naphthyl ester p-toluenesulfonate In 15 ml of DMF were dissolved 920 mg of benzoyl-L-leucyl-L-alanine and 2.05 g of $N^\delta$, $N^\omega$-dibenzyloxycarbonyl-L-arginine 1-naphthyl ester trifluoroacetate, after which 742 mg of DCC, 446 mg of HOBt and 0.42 ml of TEA were added to the resulting solution with ice-cooling. The resulting mixture was stirred at the same temperature for 3 hrs, and then stirred at room temperature for 24 hrs. The DCU thus precipitated was removed by filtration, and ethyl acetate was added to the filtrate, after which the resulting mixture was washed with 10% by weight citric acid, saturated aqueous sodium bicarbonate solution and saturated aqueous sodium chloride solution in this order, and then dried over anhydrous magnesium sulfate. The solvent was removed by evaporation. The residue was recrystallized three times from chloroform-diethyl ether to obtain 1.8 g (yield 70.0%) of white powder of benzoyl-L-leucyl-$N^\delta,N^\omega$-dibenzyloxycarbonyl-L-arginine 1-naphthyl ester, m.p. 178°–187° C.

IR $\nu_{max}^{KBr}$ cm$^{-1}$: 3380, 3270, 1740, 1718, 1630.

NMR δ ppm (CDCl$_3$): 0.9 (6H, d), 1.3 (3H, d), 1.5–2.2 (7H, m), 4.0 (2H, m), 4.2–5.0 (3H), m), 5.1 (2H, s), 5.2 (2H, s), 7.0–8.0 (aromatic protons).

In 15 ml of DMF was dissolved 1.28 g of the above ester, after which 200 mg of 10% Pd-C and 342 mg of p-toluenesulfonic acid monohydrate were added. The resulting mixture was stirred with ice-cooling for 3 hrs while passing hydrogen gas therethrough. The reaction mixture was filtered to remove the Pd-C, and anhydrous diethyl ether was added to the filtrate. The white powder precipitated was collected to obtain 1.0 g (yield 88%) of benzoyl-L-leucyl-L-alanyl-L-arginine 1-naphthyl ester p-toluenesulfonate, m.p. 86° C. (decomp.).

IR $\nu_{max}^{KBr}$ cm$^{-1}$: 3400, 1750, 1635.

NMR δ ppm (DMSO-d$_6$): 0.9 (6H, b,

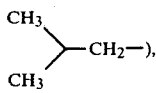

1.3 (3H, d), 1.5–2.3 (7H, b, —CH$_2$×3, —CH—), 2.3 (3H, s,

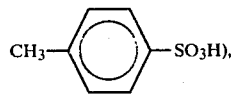

3.3 (2H, b, —CH$_2$N<), 4.6 (3H, b,

7.0–8.1 (17H, b, aromatic protons).

EXAMPLE 3

Measurement of the activity of thrombin by use of benzoyl-L-leucyl-L-alanyl-L-arginine 1-naphthyl ester as substrate To 1.7 ml of 50 mM phosphate buffer solution (pH 7.0) were added 0.1 ml of thrombin at various concentrations and 0.2 ml of benzoyl-L-leucyl-L-alanyl-L-arginine 1-naphthyl ester solutions (1 mM) dissolved in 10% aqueous dimethylsulfoxide solution, and the resulting mixture was subjected to incubation at 25° C. for 30 min. To the mixture was thereafter added 20 microliters of 8% by weight aqueous sodium laurylsulfate solution and the mixture was cooled with ice, after which 0.2 ml of 1% FVB was added thereto. The resulting mixture was allowed to stand at 0° C. for 10 min, and 2 ml of glacial acetic acid was added thereto. The azo color formed was measured as absorbance (505 nm) by means of a spectrophotometer, thereby determining the amount of the naphthol liberated by hydrolysis with the enzyme. As a control, 0.1 ml of the same buffer solution as above but free from thrombin was substituted for the mixture of the buffer solution and the thrombin. The amount of the naphthol liberated corresponded to the activity of the enzyme.

The results of measurement of absorbance at each thrombin concentration according to the above method are shown in the accompanying drawings (Curve B). Measurement of the activity of thrombin by use of L-leucyl-L-alanyl-L-arginine 1-naphthyl ester was carried out in the same manner as described for benzoyl-L-leucyl-L-alanyl-L-arginine 1-naphthyl ester (Curve A).

COMPARATIVE EXAMPLE 1

Measurement of the activity of thrombin by use of Nα-tosyl-L-arginine methyl ester as substrate To 0.1 ml of thrombin were added 0.3 ml of Nα-tosyl-L-arginine methyl ester solution (10 micromoles/0.4 ml of 5% DMSO) and 0.6 ml of 20 mM phosphate buffer solution (pH 7.4), and the resulting mixture was subjected to incubation at 37° C. for 30 min, after which 1.5 ml of a hydroxylamine solution (a mixture of equal amounts of 2 M NH$_2$OH hydrochloride and 3.5 M NaOH) was added thereto. The resulting mixture was allowed to stand at room temperature for 15 min. Thereto were added 1 ml of 18% by weight trichloroacetic acid solution, 1 ml of 4 N hydrochloric acid, and 1 ml of 10% by weight ferric chloride solution. The resulting mixture was thoroughly stirred and then centrifuged at 3,000 r.p.m. for 10 min. The color thus developed of the supernatant was measured as absorbance (530 nm) by means of a spectrophotometer. The value obtained corresponds to the amount of the substrate remaining unhydrolyzed with thrombin, and therefore, the activity of the enzyme corresponds to the difference between the value obtained when no enzyme was used (control) and the value obtained after the enzyme reaction. (Curve C).

What is claimed is:

1. A leucylalanylarginine derivative represented by the formula,

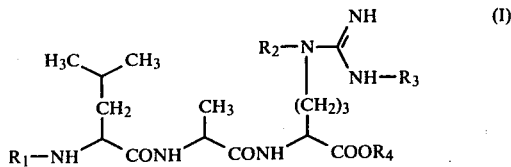

wherein R$_1$ represents hydrogen or an amino-protecting group; R$_2$ and R$_3$ represent hydrogen or guanidino-protecting groups; and R$_4$ represents naphthyl.

2. A leucylalanylargine derivative according to claim 1, wherein R$_1$ is hydrogen.

3. A leucylalanylarginine derivative according to claim 1, wherein R$_1$ is acetyl, benzoyl or benzyloxycarbonyl.

4. A leucylalanylarginine derivative according to claim 2 or 3, wherein R$_2$ and R$_3$ are benzyloxycarbonyl.

5. L-leucylalanyl-L-arginine 1-naphthyl ester.

6. Benzoyl-L-leucylalanyl-L-arginine 1-naphthyl ester.

* * * * *